United States Patent [19]

Lesher et al.

[11] Patent Number: 5,075,319

[45] Date of Patent: Dec. 24, 1991

[54] PYRIDINYL-QUINOLONE COMPOUNDS, THEIR PREPARATION AND USE

[75] Inventors: George Y. Lesher, Schodack; Baldev Singh, East Greenbush; Michael Reuman, Rensselaer, all of N.Y.

[73] Assignee: Sterling Drug Inc., New York, N.Y.

[21] Appl. No.: 405,993

[22] Filed: Sep. 13, 1989

Related U.S. Application Data

[63] Continuation-in-part of Ser. No. 219,124, Jul. 15, 1988, abandoned, which is a continuation-in-part of Ser. No. 94,359, Sep. 8, 1987, abandoned.

[51] Int. Cl.$^5$ .................... A61K 31/47; C07D 401/04
[52] U.S. Cl. .......................... 514/312; 546/4; 546/156; 560/35; 560/38; 560/51
[58] Field of Search ........................ 546/156; 514/312

[56] References Cited

U.S. PATENT DOCUMENTS

| | | | |
|---|---|---|---|
| 3,753,993 | 8/1973 | Lesher et al. | 260/286 |
| 3,907,808 | 9/1975 | Lesher et al. | 546/156 |
| 4,571,396 | 2/1986 | Hutt et al. | 546/156 |
| 4,623,650 | 11/1986 | Gilligan et al. | 514/312 |
| 4,636,506 | 1/1987 | Gilligan et al. | 514/256 |
| 4,638,067 | 1/1987 | Culbertson et al. | 546/156 |
| 4,670,444 | 6/1987 | Grohe et al. | 514/300 |
| 4,698,350 | 10/1987 | Daum et al. | 514/312 |

FOREIGN PATENT DOCUMENTS

| | | |
|---|---|---|
| 179239 | 4/1986 | European Pat. Off. |
| 309789 | 4/1989 | European Pat. Off. |
| 166678 | 8/1985 | Japan . |

OTHER PUBLICATIONS

Wise et al, *Antimicrobial Agents and Chemotherapy*, 23, pp. 559-564 (1983).

*Primary Examiner*—Mukund J. Shah
*Assistant Examiner*—E. Bernhardt
*Attorney, Agent, or Firm*—Thomas J. Johnson; Frederik W. Stonner; Paul E. Dupont

[57] ABSTRACT

Fluorinated 1-cyclopropyl-7-(substituted-pyridinyl)-1,4-dihydro-4-oxo-3-quinolinecarboxylic acids of the formula

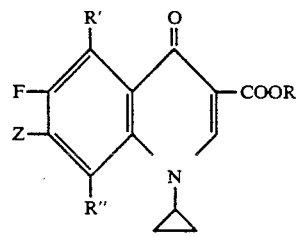

wherein R is hydrogen, R' and R" are hydrogen or fluoro, or other groups and Z is 3- or 4-pyridinyl substituted by alkyl groups or substituted alkyl groups, are superior antibacterial agents. They are prepared via a coupling reaction between the corresponding esters (R=alkyl) having a halo group in the 7-position and a substituted (trialkylstannyl)pyridine.

13 Claims, No Drawings

PYRIDINYL-QUINOLONE COMPOUNDS, THEIR PREPARATION AND USE

This application is a continuation-in-part of copending application Ser. No. 219,124, filed July 15, 1988, now abandoned, which is in turn a continuation-in-part of application Ser. No. 094,359, filed Sept. 8, 1987, now abandoned.

BACKGROUND OF THE INVENTION a) Field of the Invention

This invention relates to novel 4-oxo-3-quinolinecarboxylic acids, to methods for the preparation thereof, and compositions and methods for the use thereof as antibacterial agents.

b) Information Disclosure Statement

Antibacterially active 4-oxo-3-quinolinecarboxylic acids are known in the prior art which includes the following references.

Lesher and Carabateas U.S. Pat. No. 3,753,993, issued Aug. 21, 1973, discloses 7-(2,6-dimethyl -4-pyridinyl)-1-ethyl-1,4-dihydro-4-oxo-3-quinolinecarboxylic acid.

Sterling Drug Inc. European Patent Application, published Apr. 30, 1986 under No. 179,239, discloses 7-(2,6-dimethyl-4-pyridinyl)-1-ethyl-6-fluoro-1,4-dihydro-4-oxo-3-quinolinecarboxylic acid.

Grohe et al. U.S. Pat. No. 4,670,444, issued June 2, 1987 (Bayer AG European Patent 78,362, published May 11, 1983) discloses 1-cyclopropyl-6-fluoro-7-(1-piperazinyl)-1,4-dihydro-4-oxo-3-quinolinecarboxylic acid, also known under the generic name ciprofloxacin.

Gilligan et al. U.S. Pat. No. 4,636,506, issued Jan. 13, 1987, discloses compounds of the formula

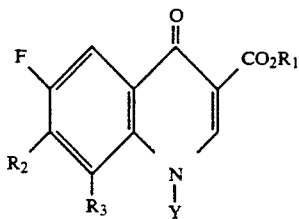

wherein $R_1$ is hydrogen, a pharmaceutically acceptable cation or alkyl of 1 to 3 carbon atoms;

Y is selected from the group consisting of alkyl and haloalkyl of 1 to 3 carbon atoms, allyl, vinyl, cyclopropyl, hydroxyethyl, phenyl, 4-hydroxyphenyl and 4-fluorophenyl;

$R_2$ is 3-pyridyl or 4-pyridyl which may be substituted by one or two substituents selected from the group consisting of fluoro, chloro, hydroxy, alkoxy of 1 to 4 carbon atoms, amino, dialkylamino of 2 to 8 carbon atoms, hydroxyalkyl of 1 to 6 carbon atoms, aminoalkyl of 1 to 6 carbon atoms; 5-pyrimidyl, or 6-quinolyl, and $R_3$ is fluoro;

and the acid addition salts thereof when $R_1$ is hydrogen. Example 1 of the patent discloses the preparation of 6,8-difluoro-1-ethyl-7-(4-pyridinyl)-4-oxo-3-quinolinecarboxylic acid.

SUMMARY OF THE INVENTION

In a product aspect, the invention relates to compounds of the formula:

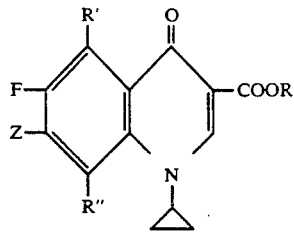

wherein:

R is hydrogen or lower-alkyl;

R' is selected from the group consisting of hydrogen, fluoro and —SR''', where R''' is phenyl, benzyl or lower-alkyl;

R" is selected from the group consisting of hydrogen, fluoro and —SR''', with the proviso that when R" is hydrogen, R' is also hydrogen;

Z is 3-pyridinyl or 4-pyridinyl substituted by from one to three lower-alkyl groups or an N-oxide thereof; or a group of the formula

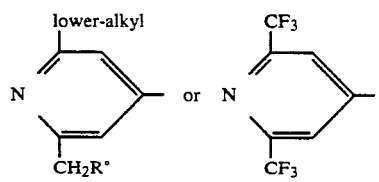

where R° is acetoxy, hydroxy, chloro, amino, lower-alkylamino, di-lower-alkylamino or lower-alkoxy;

and to pharmaceutically acceptable acid-addition salts thereof; and alkali metal or amine salts of compounds where R is hydrogen.

Especially preferred are the compounds of Formula I wherein R is hydrogen and R' and R" are hydrogen or fluoro, which compounds have outstanding antibacterial activity.

In a further product aspect the invention relates to compositions for combating bacteria which comprise an antibacterially effective amount of a compound of Formula I where R is hydrogen in admixture with a suitable carrier or diluent.

In a process aspect, the invention relates to a process for preparing a compound of Formula I where R is hydrogen and R' is hydrogen or fluoro which comprises:

(a) reacting a compound of the formula:

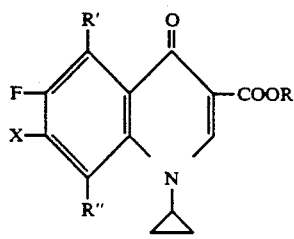

wherein R is lower-alkyl, R' is hydrogen or fluoro, R" is hydrogen or fluoro and X is chlorine, bromine or iodine, with a compound of the formula:

$$Z—Sn—(Alk)_3$$

wherein Alk is alkyl of 1-6 carbon atoms, in the presence of a palladium complex; and (b) hydrolyzing the resulting ester where X is replaced by Z.

In a further process aspect, the invention relates to a process for preparing a compound of Formula I where R and R' are hydrogen which comprises:

(a) reacting a compound of Formula I where R is alkyl of 1-6 carbon atoms and R' is fluoro, with a sulfide, R'''SH, where R''' has the previously given meaning, in the presence of sodium hydride to produce a compound according to Formula I where R' is —SR'''; and (b) heating the latter compound with Raney nickel to replace the —SR''' group by hydrogen.

In a still further process aspect, the invention relates to a process for preparing a compound of Formula I where R is hydrogen and R° is hydroxy, which comprises reacting a compound of Formula I where R is lower-alkyl and Z is

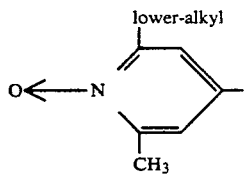

with acetic anhydride to produce a compound wherein R° is acetoxy and hydrolyzing the latter with acid or base.

In a still further process aspect, the invention relates to a process for preparing a compound of Formula I wherein R is hydrogen and R° is amino, lower-alkylamino, di-lower-alkylamino or lower-alkoxy, which comprises reacting a compound of Formula I wherein R is lower-alkyl and R° is chloro with ammonia, a lower-alkylamine, a di-lower-alkylamine or an alkali metal lower-alkoxide, respectively, and hydrolyzing the resulting ester to the free carboxylic acid.

In a still further process aspect, the invention relates to a method of combating bacteria which comprises contacting the locus of said bacteria, including administration to a mammalian host, with a composition containing an antibacterially effective amount of a compound of Formula I where R is hydrogen.

DETAILED DESCRIPTION INCLUSIVE OF PREFERRED EMBODIMENTS

In the definitions of R, R''' and Z in Formula I above, the term "lower-alkyl" stands for alkyl preferably having one to six carbon atoms which may be straight or branched.

The invention also contemplates pharmaceutically acceptable acid-addition salts of the compounds of Formula I. The nature of the acid-addition salt is immaterial provided it is derived from an acid the anion of which is essentially innocuous to animal organisms. Examples of appropriate acid-addition salts include the hydrochloride, hydrobromide, sulfate, methanesulfonate, maleate, citrate, tartrate, p-toluenesulfonate, cyclohexanesulfamate, and the like.

The compounds of Formula I where R' is hydrogen can also be prepared and used in the form of their alkali metal or amine salts, preferably the sodium, potassium, ethylenediamine or N-methylglucamine salts.

The compounds of Formula I are prepared according to the following flow sheets:

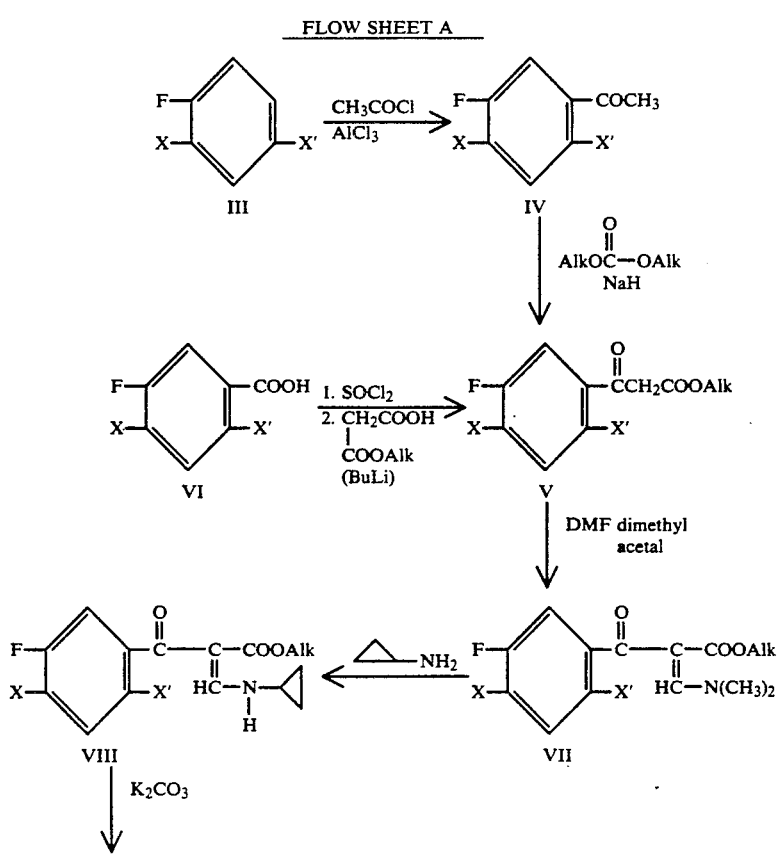

FLOW SHEET A

-continued

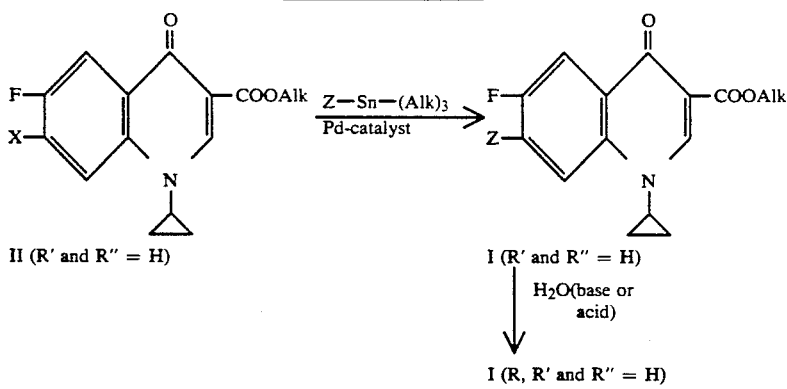

The above Flow Sheet A illustrates the preparation of 1-cyclopropyl-7-(Z)-6-fluoro-1,4-dihydro-4-oxo-3-quinolinecarboxylic acid (I; R, R' and R"=H). A 2,4-dihalofluorobenzene (III; X=Cl, Br or I, X'=F, Cl, Br or I) is subjected to a Friedel-Crafts reaction with acetyl chloride in the presence of aluminum chloride to give the corresponding halo substituted acetophenone (IV). The latter is caused to react with a dialkyl carbonate (Alk=alkyl of 1-6 carbon atoms) in the presence of sodium hydride to give an alkyl benzoylacetate of Formula V. The compound of Formula V can alternatively be prepared from a 3-fluoro-4,6-dihalobenzoic acid (VI) by first converting the latter to its acid chloride with thionyl chloride and treating the acid chloride with a half ester of malonic acid in the presence of butyllithium. The benzoylacetate (V) is then treated with dimethylformamide (DMF) dimethyl acetal [(CH$_3$)$_2$NCH(OCH$_3$)$_2$] to form a 3-dimethylaminopropenoate (VII). The latter is then treated with cyclopropylamine to produce the corresponding 3-cyclopropylaminopropenoate (VIII). Cyclization of VIII is carried out by heating in the presence of a base, preferably potassium carbonate, to give a compound of Formula II (R' and R"=H). The 1-cyclopropyl-6-fluoro-8-halo-1,4-dihydro-4-oxo-3-quinolinecarboxylate (II) is then caused to react with a (trialkylstannyl)pyridine of the formula Z—Sn—(Alk)$_3$ in the presence of a palladium complex catalyst, thereby producing an ester of Formula I where R' and R"=H. The latter can then be converted to the free acid (I; R, R' and R"=H) by a conventional hydrolysis reaction with base or acid.

In the conversion of II to I, the process is carried out using approximately equimolar amounts of II and the organotin compound in an inert solvent at a temperature between about 50° C. and 100° C., conveniently at the reflux temperature of the solvent. The reaction is complete in a period ranging from 1-24 hours. Alternatively, the reactants and catalyst can be heated in a pressurized vessel in an inert atmosphere (e.g. argon, nitrogen) at a temperature between about 125° and 175° C. until the reaction is complete (1-5 hours). The palladium complex catalyst, present to the extent of about 5 mole percent, can be any such catalyst known to effect crosscoupling of organotin compounds with organic halides [cf. Kosugi et al., Bull. Chem. Soc. Japan 59, 677-679 (1986)], for example, PdCl$_2$(PPh$_3$)$_2$, Pd(PPh$_3$)$_4$, PdCl$_2$[P(o-tolyl)$_3$]$_2$, PdCl$_2$+2P(OEt)$_3$ and PdCl$_2$(PhCN)$_2$. A preferred catalyst is dichlorobis(triphenylphosphine)palladium [PdCl$_2$(PPh$_3$)$_2$].

FLOW SHEET B

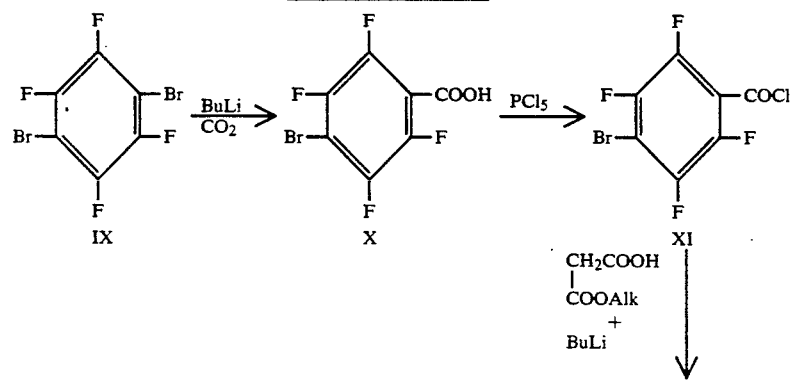

FLOW SHEET B

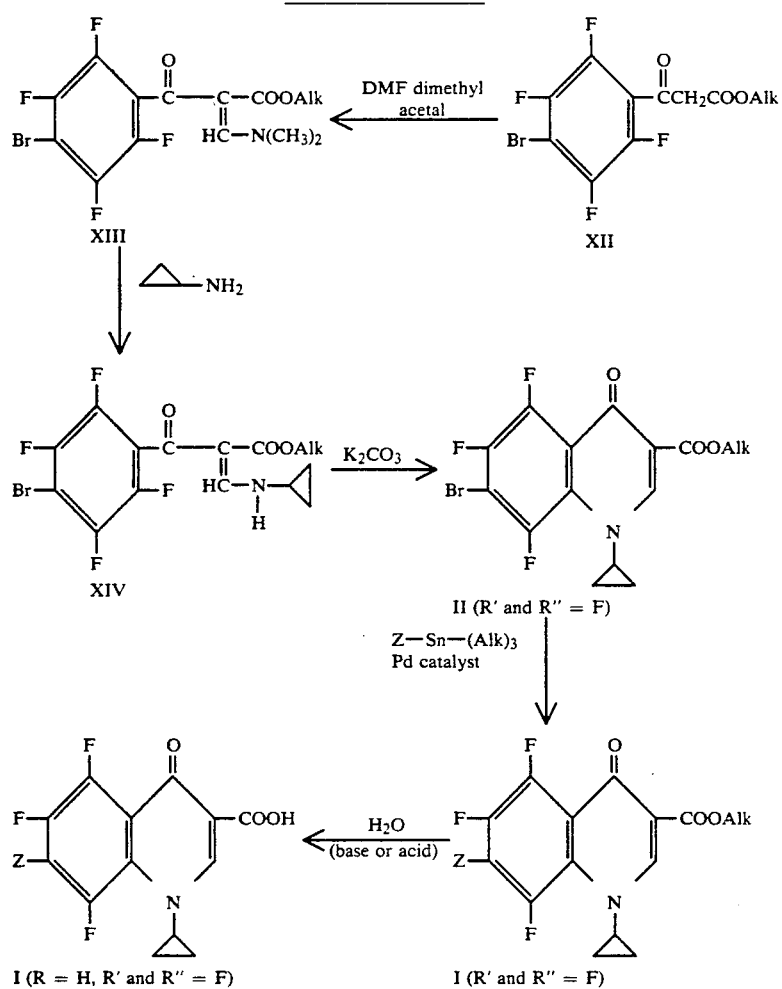

The above Flow Sheet B illustrates the preparation of 1-cyclopropyl-7-(Z)-5,6,8-trifluoro-1,4-dihydro-4-oxo-3-quinolinecarboxylic acid (I; R=H, R' and R''=F). 1,4-Dibromo-2,3,5,6-tetrafluorobenzene (IX) is metalated with butyllithium and then caused to react with carbon dioxide to give 4-bromo-2,3,5,6-tetrafluorobenzoic acid (X). The latter is converted to its acid chloride (XI) which reacts with a half ester of malonic acid in the presence of butyllithium to afford an alkyl 4-bromo-2,3,5,6-tetrafluorobenzoylacetate (XII). A series of transformations (XII→XIII→XIV→II) entirely analogous to the sequence V→; VII→VIII→II in Flow Sheet A affords an alkyl 7-bromo-1-cyclopropyl-5,6,8-trifluoro-1,4-dihydro-3-quinolinecarboxylate (II; R' and R''=F). Reaction of the latter with Z—Sn—(Alk)$_3$ in the presence of a palladium complex catalyst gives I (R=alkyl, R' and R''=F) which is readily hydrolyzed to the free acid I (R=H, R' and R''=F).

FLOW SHEET C

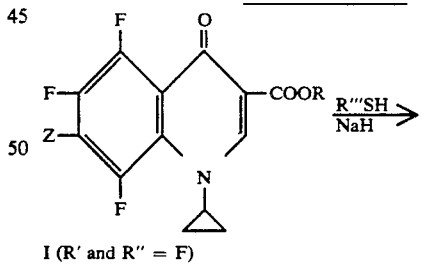

I (R' and R'' = F)

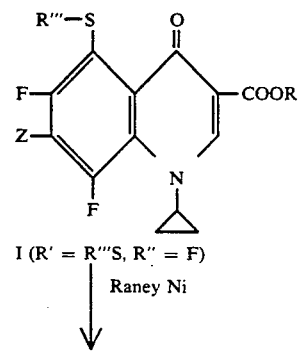

I (R' = R'''S, R'' = F)

Raney Ni

-continued
FLOW SHEET C

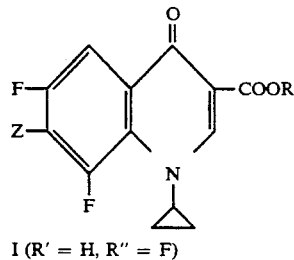

I (R' = H, R" = F)

The above flow sheet illustrates the preparation of 1-cyclopropyl-6,8-difluoro-1,4-dihydro-7-(Z)-4-oxo-3-quinolinecarboxylic acid (I; R and R'=H, R"=F). The process involves the replacement of the 5-fluoro substituent by hydrogen in the 5,6,8-trifluoro compound prepared according to Flow Sheet B. The reactions can be carried out either on the ester (R=alkyl) or free acid (R=H). The trifluoro compound (I; R' and R"=F) is caused to react with a thiol (R'''SH, R'''=alkyl, benzyl or phenyl) in the presence of sodium hydride to give a corresponding compound where the 5-fluoro substituent is replaced by R'''-S. When the latter compound is heated with Raney nickel in a solvent such as ethanol, the thiol group is removed to give I (R'=H, R"=F). In some cases there is some tendency for the 8-fluoro group also to be replaced by thiol leading to a mixture of products which, however, are readily separated by fractional crystallization or chromatography.

An alternative approach to the preparation of I (R'=H, R"=F'), which avoids the removal of the eventual 5-fluoro substituent according to Flow Sheet C, is accomplished starting with the commercially available 2,3,4,5-tetrafluorobenzoic acid following the sequence of reactions outlined in Flow Sheet D below.

FLOW SHEET D

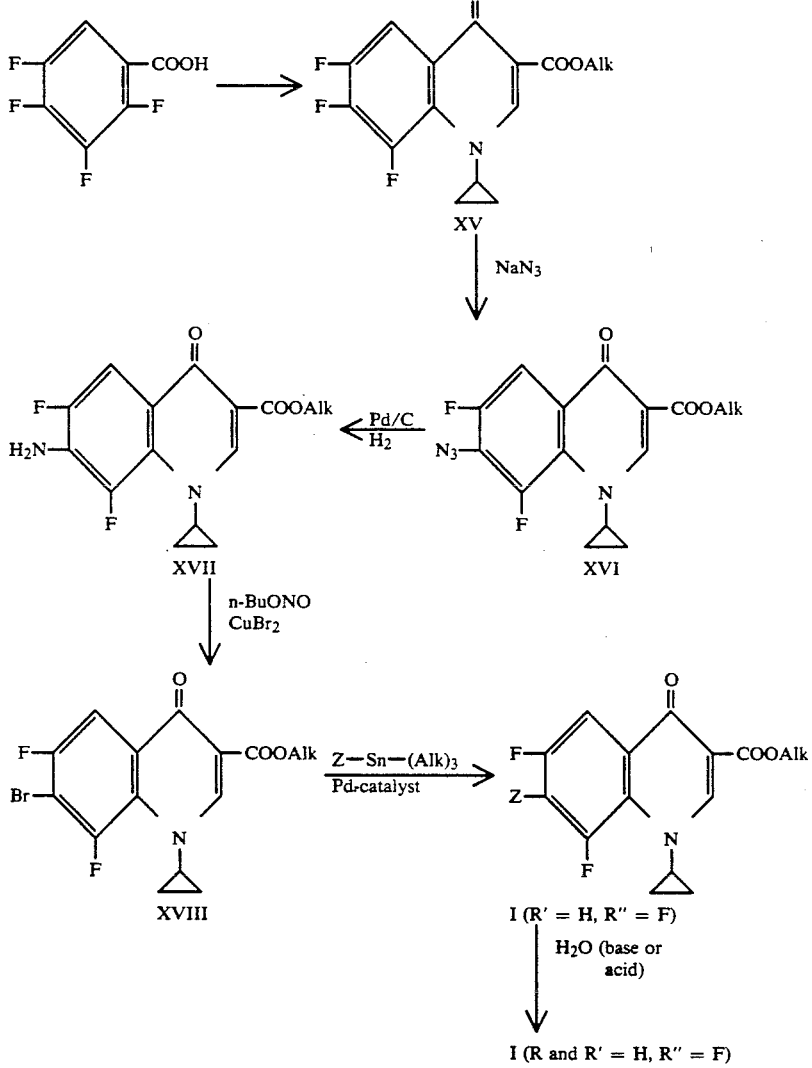

Compound XV is produced from 2,3,4,5-tetrafluorobenzoic acid by a series of steps corresponding to the sequence VI→V→VII→VIII→II on Flow Sheet A. In order to replace the 7-fluoro group by bromine prior to the tin-coupling reaction, compound XV is caused to react with sodium azide to give the 7-azido compound XVI. The latter is hydrogenated in the presence of palladium-on-carbon to form the 7-amino compound XVII which is converted to the 7-bromo compound XVIII by reaction with n-butyl nitrite and cupric bromide. The tin-coupling reaction with Z—Sn—(Alk)$_3$ produces the ester of the desired compound of Formula I where R'=H and R''=F.

A further alternative approach to the preparation of I (R' and R''=H) uses 2,4-dichloro-5-fluorobenzoic acid as starting material. The latter can be converted according to the transformations of Flow Sheet A to ethyl 7-chloro-1-cyclopropyl-6-fluoro-1,4-dihydro-4-oxo-3-quinolinecarboxylate, which can be coupled directly with Z—Sn—(Alk)$_3$.

An alternative synthetic approach may be used to prepare compounds of Formula I where in the definition of Z, R° is a functional group as defined above. This is carried out starting with the N-oxide of a compound of Formula I where R is lower-alkyl and Z is

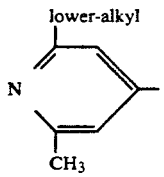

prepared by conventional peracid oxidation. Said N-oxide is caused to react with acetic anhydride, heated at reflux, to form a compound where R° is acetoxy. Hydrolysis of the latter by heating with hydrochloric acid gives a compound where R° is hydroxy and R is hydrogen. The compound where R° is hydroxy in the form of its ester (R=lower-alkyl) reacts with thionyl chloride, heated at reflux to form a compound where R° is chloro which serves as a common intermediate for compounds where R° is amino, lower-alkylamino, di-lower-alkylamiino or lower-alkoxy by reaction, respectively, with ammonia, a lower-alkylamine, a di-lower-alkylamine or an alkali metal lower-alkoxide. The reaction with ammonia or an amine takes place in an inert solvent at room temperature. The reaction with an alkoxide takes place in an inert solvent at a temperature of 50°-100° C.

The structures of the compounds were established by the modes of synthesis, by elementary analyses and by infrared, nuclear magnetic resonance and/or mass spectra.

The following examples will further illustrate the invention.

EXAMPLE 1 a) 4-Bromo-2,5-difluoroacetophenone [IV; X=Br, X'=F]

To a stirred mixture of 20 g 2,5-difluorobromobenzene and 35.2 g aluminum chloride under nitrogen at 60° C. was added dropwise 11.2 ml acetyl chloride. The reaction mixture was stirred at 95° C. for 90 min. and then poured over 250 g ice followed by 17 ml concentrated hydrochloric acid. The aqueous mixture was extracted with ether, and the extracts washed with sodium chloride solution and concentrated. The residue (23.6 g) was distilled in vacuo to give 18.4 g (76%) 4-bromo-2,5-difluoroacetophenone, b.p. 65° C. (0.1 mm).

b) Ethyl 4-bromo-2,5-difluorobenzoylacetate [V; Alk=C$_2$H$_5$, X=Br, X'=F]

To a stirred mixture of 18 g 4-bromo-2,5-difluoroacetophenone and 233 ml diethyl carbonate cooled in an ice-bath was slowly added 6.4 g sodium hydride (60% in oil). The reaction mixture was heated at 80° C. for 90 min. and then added to 700 ml ice containing 25 ml acetic acid. The aqueous mixture was extracted with ether, and the ether extracts were washed with sodium chloride solution, dried (magnesium sulfate) and concentrated. The residue was distilled, collecting the material (15.33 g) boiling at 85°-135° C. (0.05 mm). The latter material was chromatographed on 185 g silica gel (Kieselgel 60) using 20% ether in hexane as eluant to give 6.69 g ethyl 4-bromo-2,5-difluorobenzoylacetate as the first product to be eluted.

c) Ethyl 4-bromo-2,5-difluorobenzoylacetate [V; Alk=C$_2$H$_5$, X=Br, X'=F]

A solution of 37 g monoethyl malonate and 18 mg 2,2'-biquinoline in 775 ml dry tetrahydrofuran was cooled to −30° C. under nitrogen. To this solution was added dropwise 215.6 ml 2.6M n-butyllithium in hexane. The reaction mixture was allowed to warm to −5° C., then cooled to −30° C. and another 20 ml butyllithium was added. Repetition of the procedure with another 5 ml butyllithium completed the metalation of the monoethyl malonate. The resulting reagent mixture was cooled to −50° C. and 4-bromo-2,5-difluorobenzoyl chloride (prepared from 22.28 g 4-bromo-2,5-difluorobenzoic acid and thionyl chloride) was added dropwise. The reaction mixture was then stirred at room temperature for 1 hour, then cooled and 750 ml 1N hydrochloric acid was added. The aqueous mixture was extracted with ether, and the extracts were washed with saturated sodium bicarbonate and sodium chloride solutions, dried (magnesium sulfate) and concentrated. The residue crystallized from hexane to give 21.0 g ethyl 4-bromo-2,5-difluorobenzoylacetate, m.p. 51°-53° C.

d) Ethyl 2-(4-bromo-2,5-difluorobenzoyl)-3-dimethylaminopropenoate [VII; Alk=C$_2$H$_5$, X=Br, X'=F]

To a stirred solution of 2.17 g ethyl 4-bromo-2,5-difluorobenzoylacetate in 5 ml tetrahydrofuran was added 0.94 ml dimethylformamide dimethyl acetal. The reaction mixture was stirred at room temperature for 24 hours and then concentrated in vacuo to give 2.63 g of an orange oil which was used directly in the next reaction.

e) Ethyl 2-(4-bromo-2,5-difluorobenzoyl)-3-cyclopropylaminopropenoate [VIII; Alk=C$_2$H$_5$, X=Br, X'=F]

The product of part (d) above was dissolved in 10 ml tetrahydrofuran and cooled in an ice-bath. Cyclopropylamine (0.5 ml) was added and the reaction mixture was stirred at 0° C. for 1 hour. The mixture was concentrated in vacuo to give 2.52 g of an orange oil which was used directly in the next reaction.

f) Ethyl 7-bromo-1-cyclopropyl-6-fluoro-1,4-dihydro-4-oxo-3-quinolinecarboxylate [II; R=C$_2$H$_5$, R' and R''=H, X=Br]

A mixture of the product of part (e) and 1.8 g potassium carbonate in 10 ml dimethylformamide was heated at 100° C. (steam bath) for 1 hour. The reaction mixture was added to water and the product was collected by filtration, dried, and recrystallized from ethanol to give 1.2 g ethyl 7-bromo-1-cyclopropyl-6-fluoro-1,4-dihydro-4-oxo-3-quinolinecarboxylate, m.p. 251°-253° C.

g) 2,6-Dimethyl-4-(trimethylstannyl)pyridine

To a mixture of 100 g sodium (30% dispersion in toluene) and 400 ml dimethoxyethane (DME) cooled in an ice-salt bath and under nitrogen was added a solution of 121 g trimethyltin chloride in 50 ml DME over a 2 hour period while keeping the temperature below 5° C. The mixture was stirred at 0°–5° C. for 2.5 hours and then 70 g 4-chloro-2,6-dimethylpyridine in 50 ml DME was added over a 1.5 hour period while keeping the temperature at 0°–10° C. The reaction mixture was stirred at the latter temperature for 1 hour and then allowed to stand at room temperature overnight. The mixture was filtered and concentrated, and the residue treated with ether and again filtered and concentrated. The resulting orange liquid was distilled, collecting the material boiling at 130° C. (20 mm) to give 80 g 2,6-dimethyl-4-(trimethylstannyl)pyridine.

The starting material, 4-chloro-2,6-dimethylpyridine, was prepared by heating (8 hours at reflux) 2,6-lutidine-N-oxide hydrochloride with phosphorus oxychloride. The crude product, a mixture of 4-chloro-2,6-dimethylpyridine and 2-chloromethyl-6-methylpyridine, was purified by heating it with triethylamine in ethanol whereby the byproduct was converted to its triethyl quaternary ammonium salt (monohydrate, m.p. 103°–104° C.) which was readily separated from the desired 4-chloro-2,6-dimethylpyridine by aqueous extraction. In this way a 56.6% yield of 4-chloro-2,6-dimethylpyridine (b.p. 71°–73° C., 15 mm.) from the N-oxide was obtained.

h) Ethyl 1-cyclopropyl-7-(2,6-dimethyl-4-pyridinyl)-6-fluoro-1,4-dihydro-4-oxo-3-quinolinecarboxylate [I; R=$C_2H_5$, R' and R''=H, Z=2,6-dimethyl-4-pyridinyl]

2,6-Dimethyl-4-(trimethylstannyl)pyridine (part g) (10.1 g) and 1.52 g dichlorobis(triphenylphosphine)palladium was added to a stirred solution of 12.13 g ethyl 7-bromo-1-cyclopropyl-6-fluoro-1,4-dihydro-4-oxo-3-quinolinecarboxylate (part f) and 10 ml hexamethylphosphoramide (HMPA) in 240 ml dioxane under nitrogen. The reaction mixture was heated under reflux for 24 hours, then cooled and partitioned between water and methylene dichloride. The organic extract was washed with sodium chloride solution, dried (magnesium sulfate) and concentrated to give 12.0 g ethyl 1-cyclopropyl-7-(2,6-dimethyl-4-pyridinyl)6-fluoro-1,4-dihydro-4-oxo-3-quinolinecarboxylate, m.p. 198°–200° C.

i) 1-Cyclopropyl-7-(2,6-dimethyl-4-pyridinyl)-6-fluoro1,4-dihydro-4-oxo-3-quinolinecarboxylic acid [I; R, R' and R''=H, Z=2,6-dimethyl-4-pyridinyl]

A suspension of 12.4 g ethyl 1-cyclopropyl-7-(2,6-dimethyl-4-pyridinyl)-6-fluoro-1,4-dihydro-4-oxo-3-quinolinecarboxylate in 320 ml water containing 3.5 g sodium hydroxide was heated at reflux for 2.5 hours. The reaction mixture was then decolorized with charcoal, filtered and brought to pH 5–5.5 with acetic acid. The solid that precipitated was collected, dried in vacuo and recrystallized from dimethylformamide to give 8.4 g 1-cyclopropyl-7-(2,6-dimethyl-4-pyridinyl)-6-fluoro-1,4-dihydro-4-oxo-3-quinolinecarboxylic acid, m.p. 300°–302° C. (decompn.).

A 2.50 g sample of the product was heated with 10 ml ethylenediamine to 50°–60° C., then cooled to room temperature and the solid product isolated and dried to give 1.80 g of the ethylenediamine salt monohydrate, yellowish powder, m.p. 303°–305° C.

EXAMPLE 2 a) 2,4-Dichloro-5-fluoroacetophenone [IV; X and X'=Cl] was prepared from 49.5 g 2,4-dichlorofluorobenzene and 33 g acetyl chloride in the presence of 102 g aluminum chloride according to the procedure described in Example 1, part (a), and was obtained in 55% yield as a liquid, b.p. 89°–90° C. (2.5 mm.).

b) Ethyl 2,4-dichloro-5-fluorobenzoylacetate [V; Alk=$C_2H_5$, X and X'=Cl] was prepared from 50 g 2,4-dichloro-5-fluoroacetophenone and diethylcarbonate in the presence of sodium hydride according to the procedure described in Example 1, part (b), and was obtained in 47% yield as a liquid, b.p. 125°–135° C. (0.25 mm.).

c) Ethyl 2-(2,4-dichloro-5-fluorobenzoyl)-3-dimethylaminopropenoate [VII; Alk=$C_2H_5$, X and X'=Cl] was prepared from 10 g ethyl 2,4-dichloro-5-fluorobenzoylacetate and 5 ml dimethylformamide dimethylacetal according to the procedure of Example 1, part (d), and the crude product used directly in the next reaction.

d) Ethyl 2-(2,4-dichloro-5-fluorobenzoyl)-3-cyclopropylaminopropenoate [VIII; Alk=$C_2H_5$, X and X'=Cl] was prepared from the crude product of part (c) and 2.24 g cyclopropylamine according to the procedure of Example 1, part (e), and the crude product used directly in the next reaction.

e) Ethyl 7-chloro-1-cyclopropyl-6-fluoro-1,4-dihydro-4-oxo-3-quinolinecarboxylate [II; R=$C_2H_5$, R' and R''=H, X=Cl] was prepared from the crude product of part (c) and 9.88 g potassium carbonate according to the procedure of Example 1, part (f) to give 7.0 g of solid product (63% overall yield from the ethyl 2,4-dichloro-5-fluorobenzoylacetate of part (b)).

f) 1-Cyclopropyl-7-(2,6-dimethyl-4-pyridinyl)-6-fluoro-1,4-dihydro-4-oxoquinolinecarboxylic acid [I; R, R' and R''=H, Z=2,6-dimethyl-4-pyridinyl]

Ethyl 7-chloro-1-cyclopropyl-6-fluoro-1,4-dihydro-4-oxo-3-quinolinecarboxylate (3.0 g) was caused to react with 3.0 g 2,6-dimethyl-4-(trimethylstannyl)pyridine in the presence of 435 mg dichlorobis(triphenylphosphine)palladium in dioxane medium according to the procedure of Example 1, part (h). The crude product in methanol solution was chromatographed on 100 g silica gel and eluted with 5–20% methanol in ether. The fractions containing the desired ethyl ester were combined and hydrolyzed with 50 ml 3N hydrochloric acid on a steam bath for 3.5 hours. The reaction mixture was cooled, extracted with chloroform and the aqueous layer concentrated to dryness. The residue was made basic with 10% aqueous potassium carbonate, filtered and acidified with acetic acid. The solid product was collected and dried to give 1.6 g 1-cyclopropyl-7-(2,6-dimethyl-4-pyridinyl)-6-fluoro-1,4-dihydro-4-oxoquinolinecarboxylic acid, m.p. 302°–303° C., identical with the final product of Example 1.

EXAMPLE 3 a) 1,4-Dibromo-2,5-difluorobenzene

A 5 L flask was charged with methylene chloride (2.15 L). The vessel was placed under a nitrogen atmosphere and aluminum bromide (100 g, 0.37 m) was added with stirring to form a solution. 1,4-Difluorobenzene (901 ml, 8.76 m) and bromine (898 ml, 17.43 m) were added in portions over a period of 4.5 hours.

The reaction was stirred overnight and then heated to 40° C. for thirty minutes to expel most of the gaseous hydrogen bromide. The cooled solution was quenched into water (12 L) with rapid stirring. The lower layer was removed and concentrated at atmospheric pressure on a steam bath. When most of the methylene chloride had been removed, hexane (500 ml) was added and the distillation was continued until a head temperature of 65° C. was reached. The residue was diluted was hexane (2 L) and cooled to −5° C. using a Dry Ice/isopropanol bath. The resulting white solid was collected and washed with 500 ml of cold (−30° C.) hexane. Two additional crops were obtained by cooling the mother liquors to −20° and −40° C. respectively. The low melting solids were dried for 16 hours at room temperature in vacuo. The first two crops totaling 1424 g (59.8% yield) were pure enough (>98%) to be carried forward.

b) 4-Bromo-2,5-difluorobenzoic acid [VI; X=Br, X'=F]

To a cold (−60° C.) solution of 1,4-dibromo-2,5-difluorobenzene (700 g, 2.56 moles) in anhydrous ether (10 L) under nitrogen was added a cold (−60° C.) dilute solution of n-butyllithium in hexane [1.70 L (2.7 moles) of 1.6M n-butyllithium in hexane diluted with an additional 4.8 L of hexane] over a two hour period. Dry Ice (0.5 kg) was added to produce a white precipitate and the temperature rapidly rose to −35° C. before falling back to −50° C. The slurry was allowed to stand overnight at ambient temperature. The reaction mixture was quenched into 1.2M HCl (4 L) and the organic layer was washed with water before being concentrated to a solid. Hexane (1.5 L) was added and the resulting slurry was cooled to 5° C. and filtered. The filter cake was washed with cold hexane and air dried to afford 440 g of crude product (73% yield) which was used directly in the next step.

c) 4-Bromo-2,5-difluorobenzoyl chloride

A total of 2075 g (8.79 moles) of crude 4-bromo-2,5-difluorobenzoic acid from step (b) was treated with thionyl chloride (2.0 L), and the resulting slurry was slowly heated to reflux (90° C. internal) to obtain a solution. After removal of excess thionyl chloride, the product was collected at 85°–95° C. (oil pump, vacuum not measured), leaving a solid residue. The distillate afforded 2045 g (91%) of a liquid which was used directly in the next step.

d) Ethyl 4-bromo-2,5-difluorobenzoylacetate [V; Alk=Et, X=Br, X'=F]

A solution of monoethyl malonate (800 g, 6.06 moles) and 3 g of 2,2'-bipyridyl (indicator) in tetrahydrofuran (11.0 L) was cooled in a Dry Ice/acetone bath while adding n-butyllithium in hexane (7.50 L, 1.6M) until a reddish color persisted for several minutes at −15° C. The reaction mixture was then cooled to −60° C. and 4-bromo-2,5-difluorobenzoyl chloride (785 g, 3.07 moles) was added over a 1¼ hour period. Stirring was continued for ½ hour before quenching the reaction into 16 L of 1N hydrochloric acid. The organic layer was washed with 2×10 L of water, 2×6 L of 10% aqueous sodium bicarbonate, and then 2×10 L of water. Concentration of the organic layer to dryness afforded an oil which crystallized on cooling. The concentrates from three runs (total of 8.0 moles) were combined and recrystallized from 6 L of hexane to give a first crop of 1505 g (61.5%) and a second crop of 220 g (9.0%).

e) Ethyl 3-(cyclopropylamino)-2-(4-bromo-2,5-difluorobenzoyl)acrylate [VIII; Alk=Et, X=Br, X'=F]

A solution of ethyl 4-bromo-2,5-difluorobenzoylacetate (1224 g, 4.0 moles) and N,N-dimethylformamide dimethl acetal (630 ml, 4.8 moles) in 2.5 L of tetrahydrofuran was heated at reflux for 2½ hours and then stirred overnight at ambient temperature. The solvent was removed under reduced pressure and the residue was triturated with hexane to remove excess N,N-dimethylformamide dimethyl acetal. The solvent was decanted off. The residue was dissolved in 2.5 L of tetrahydrofuran and cooled to 5° C. Cyclopropylamine (305 ml, 4.4 moles) was added over a ½ hour period. The solvent was removed by vacuum distillation and the residue was used directly in the next step.

f) Ethyl 1-cyclopropyl-7-bromo-6-fluoro-1,4-dihydro-4-oxo-3-quinolinecarboxylate [II; Alk=Et, X=Br]

To the ethyl 3-(cyclopropylamino)-2-(4-bromo-2,5-difluorobenzoyl)acrylate prepared above (assuming 4.0 moles) was added N,N-dimethylformamide (2.5 L) and potassium carbonate (736 g, 5.3 moles). The mixture was heated to 90° C. on a steam bath, at which time an exothermic reaction started raising the temperature to 115° C. over 5 minutes. A thick precipitate formed. The reaction was then stirred at ambient temperature and the solids were collected at 50° C. The filter cake was washed with N,N-dimethylformamide, then slurried in 10 L of water and refiltered. The off-white solids were washed with water and dried. The crude product was purified by recrystallization from 20 volumes of methylene chloride and repeated rework of second and third crops. From 1585 g of crude product a total of 1270 g of purified material was obtained in 80% recovery.

g) 2,6-Dimethyl-4-(tributylstannyl)pyridine

A 22 L flask was charged with 740 g of 4-bromo-2,6-lutidine and 10.0 L of diethyl ether and cooled to −60° C. in a Dry Ice/acetone bath under nitrogen. A solution of 4.0 moles of n-butyllithium was added dropwise over 1 hour maintaining a temperature below −58° C. to form an orange-yellow precipitate. After continued stirring in the cold for 15 minutes, 1280 g of tributyltin chloride was added over 2 hours at a temperature of −60° to −57° C. to form a solution. The reaction was stirred cold for 45 minutes before it was slowly (2 hours) warmed to 20° C. A portion of Super-Cel (100 g) was added and the reaction mixture was filtered to remove the precipitated lithium chloride. The cake was washed with diethyl ether (2×500 mL). After concentration to dryness a total of 1575 g (99.7% yield) of product was obtained which was used without further purification. h) Ethyl 1-cyclopropyl-7-(2,6-dimethyl-4-pyridinyl)-6-fluoro-1,4-dihydro-4-oxo-3-quinolinecarboxylate [I; Alk=Et, R' and R"=H, Z=2,6-dimethyl-4-pyridinyl]

A mixture of ethyl 1-cyclopropyl-7-bromo-6-fluoro-1,4-dihydro-4-oxo-3-quinolinecarboxylate (500 g, 1.42 mole), 2,6-dimethyl-4-(tributylstannyl)pyridine (617 g, 1.56 mole) and dichlorobis(triphenylphosphine)palladium (28 g, 3 molar %) in 400 ml of N,N-dimethylformamide was slowly heated to 150° C. in a nitrogen atmosphere and maintained at that temperature for one hour. It was cooled, dissolved in 3 L chloroform and stirred with 2 L of water for 15 minutes. The two-phased solution was filtered through a bed of Super-Cel, and the organic layer was separated and dried over anhydrous magnesium sulfate. The solvent was removed under reduced pressure and the residue was stirred with 3 L of ether for 25-30 minutes. It was filtered and washed with more ether (2 L). The solids were air dried inside the hood to give 430 g (80%) of product, used directly in the next reaction.

i) 1-Cyclopropyl-7-(2,6-dimethyl-4-pyridyl)-6-fluoro-1,4-dihydro-4-oxo-3-quinolinecarboxylic acid [I; R, R' and R"=H, Z=2,6-dimethyl-4-pyridinyl]

A suspension of ethyl 1-cyclopropyl-7-(2,6-dimethyl-4-pyridyl)-6-fluoro-1,4-dihydro-4-oxo-3-quinolinecarboxylate (430 g, 1.13 mole) and sodium hydroxide (115 g, 2.87 moles) in 5 L water was stirred on a steam bath for 4 hours resulting in a clear solution. The hot solution was treated with charcoal (20 g) and filtered. The yellow filtrate was cooled to room temperature and washed once with 3 L ethyl acetate to remove nonacidic impurities. The aqueous layer was then stirred with excess acetic acid (240 ml) at 60°–70° C. for one hour. The white solid was filtered hot, washed with 2 L of water and dried at 60°–70° C. under vacuum for 24 hours to afford 363 g (91%) of crude product. This material was crystallized from 8 L of N,N-dimethylformamide to yield 340 g (93.6%) of faint yellow product, m.p. 300°–301° C., identical with the product of Examples 1(i) and 2(f).

EXAMPLE 4 a) 4-Bromo-2,3,5,6-tetrafluorobenzoic acid [X]

n-Butyllithium (42 ml, 2.4M in hexane) was slowly added to a solution of 30.78 g 1,4-dibromo-2,3,5,6-tetrafluorobenzene in 200 ml tetrahydrofuran cooled to −70° C. under nitrogen. Solid carbon dioxide (about 12 g) was then added to the stirred mixture which was then allowed gradually to warm to 0° C. at which point 16 ml 6M hydrochloric acid and 16 ml water were added. The reaction mixture was concentrated and the residue extracted with methylene dichloride. The extract was washed with concentrated sodium chloride solution, dried (magnesium sulfate) and concentrated to dryness to give 22.23 g (81.5%) 4-bromo-2,3,5,6-tetrafluorobenzoic acid, m.p. 128°–135° C.

b) 4-Bromo-2,3,5,6-tetrafluorobenzoylchloride [XI]

A mixture of 21.83 g 4-bromo-2,3,5,6-tetrafluorobenzoic acid and 16.7 g phosphorus pentachloride was stirred at room temperature for about three days. The reaction mixture was then distilled under aspirator vacuum to give 20.44 g (88%) of the acid chloride.

c) Ethyl 4-bromo-2,3,5,6-tetrafluorobenzoylacetate [XII; Alk=$C_2H_5$]

n-Butyllithium (192 ml, 2.4M in hexane) was slowly added to a stirred solution of 30.24 g monoethylmalonate and 15 mg 2,2′-bipyridine in 500 ml tetrahydrofuran cooled to −60° to −70° C. under nitrogen. After about half of the butyllithium had been added, the temperature of the mixture was raised to −20° to −25° C. at which temperature the remainder of the butyllithium was added. The reaction mixture was then recooled to −60° to −70° C. and 33.41 g 4-bromo-2,3,5,6-tetrafluorobenzoyl chloride in 10 ml tetrahydrofuran was added. The reaction mixture was allowed to warm to room temperature, stirred overnight, and then poured into 460 ml 1M hydrochloric acid. The organic layer was separated, dried (magnesium sulfate) and concentrated. The residue was dissolved in ether, washed with aqueous potassium bicarbonate solution, dried (magnesium sulfate), concentrated and distilled to give 34.18 g ethyl 4-bromo-2,3,5,6-tetrafluorobenzoylacetate, b.p. 112°–117° C. (0.8 mm).

d) Ethyl 2-(4-bromo-2,3,5,6-tetrafluorobenzoyl)-3-dimethylaminopropenoate [XIII; Alk=$C_2H_5$]

Dimethylformamide dimethylacetal (11.85 g) was added to a solution of 33.63 g ethyl 4-bromo-2,3,5,6-tetrafluorobenzoylacetate in 100 ml tetrahydrofuran cooled in an ice-bath. The reaction mixture was then immersed in a warm water bath in order to drive it to completion. The resulting solution was used directly in the next reaction.

e) Ethyl 2-(4-bromo-2,3,5,6-tetrafluorobenzoyl)-3-cyclopropylaminopropenoate [XIV; Alk=$C_2H_5$]

The solution from part (d) above was cooled in an ice-bath, and 7 ml cyclopropylamine was added. The reaction mixture was concentrated, the residue dissolved in 550 ml hot absolute ethanol, and the product allowed to crystallize upon cooling to give 31.66 g ethyl 2-(4-bromo-2,3,5,6-tetrafluorobenzoyl)-3-cyclopropylaminopropenoate, m.p. 167°–168.5° C. (79% yield from ethyl 4-bromo-2,3,5,6-tetrafluorobenzoyl acetate).

f) Ethyl 7-bromo-1-cyclopropyl-5,6,8-trifluoro-1,4-dihydro-4-oxo-3-quinolinecarboxylate [II; R′ and R″=F, Alk=$C_2H_5$]

Potassium carbonate (30 g) was added to a stirred solution/suspension of 31.65 g ethyl 2-(4-bromo-2,3,5,6-tetrafluorobenzoyl)-3-cyclopropylaminopropenoate in 300 ml dimethylformamide. The mixture was heated at 150° C. for 1.5 hours, then cooled, poured into water and extracted with methylene dichloride. The extract was washed with water and sodium chloride solution, dried (magnesium sulfate) and concentrated. The residue was recrystallized from acetonitrile to give 19.3 g (64%) ethyl 7-bromo-1-cyclopropyl-5,6,8-trifluoro-1,4-dihydro-4-oxo-3-quinolinecarboxylate, m.p. 187°–189° C.

g) 1-Cyclopropyl-7-(2,6-dimethylpyridinyl)-5,6,8-trifluoro-1,4-dihydro-4-oxo-3-quinolinecarboxylic acid [I; R=H, R′ and R″=F, Z=2,6-dimethyl-4-pyridinyl]

A mixture of 2.8 g ethyl 7-bromo-1-cyclopropyl-5,6,8-trifluoro-1,4-dihydro-4-oxo-3-quinolinecarboxylate, 2.2 g 2,6-dimethyl-4-(trimethylstannyl)pyridine (Example 1, part g), 2 ml hexamethylphosphoramide, 320 mg dichlorobis(triphenylphosphine)palladium and 50 ml dioxane was stirred and heated under reflux in an argon atmosphere for 24 hours. The reaction mixture was concentrated to dryness and the residue was treated with 100 ml of 1N hydrochloric acid and heated at reflux for 2 hours. The latter mixture was filtered and the filtrate concentrated to dryness. The residue was dissolved in 50 ml 5% aqueous potassium carbonate, decolorized with charcoal and filtered. The filtrate was acidified with concentrated hydrochloric acid, sodium acetate added, and the resulting precipitate was collected, dried and recrystallized from ethanol to give 1.6 g 1-cyclopropyl-7-(2,6-dimethylpyridinyl)-5,6,8-trifluoro-1,4-dihydro-4-oxo-3-quinolinecarboxylic acid as a cream-colored solid, m.p. 264°–266° C.

EXAMPLE 5 a) Ethyl 1-cyclopropyl-6,8-difluoro-7-(2,6-dimethyl-4-pyridinyl)-5-(benzylthio)-1,4-dihydro-4-oxo-3-quinolinecarboxylate [I; R=$C_2H_5$, R′=$C_6H_5CH_2S$, R″=F, Z=2,6-dimethyl-4-pyridinyl]

Sodium hydride (1 g, 60% in oil) was added portionwise to a mixture of 7.39 g ethyl 1-cyclopropyl-7-(2,6-dimethyl-4-pyridinyl)-5,6,8-trifluoro-1,4-dihydro-4-oxo-3-quinolinecarboxylate (Example 4, part g) and 2.1 ml benzylthiol in 250 ml tetrahydrofuran cooled in an ice-bath. After the addition of sodium hydride was complete, thin layer chromatography indicated that starting material still remained; therefore, an additional 0.2 ml benzylthiol and 0.1 g sodium hydride were added. The reaction mixture was washed with water and sodium chloride solution, and the aqueous layer was extracted with ethyl acetate. The combined organic extracts were dried (sodium sulfate) and concentrated. The residue was suspended in hexane and the solid product recovered (7.0 g). The latter was taken up in isopropyl acetate-methylene dichloride (1:1) and chromatographed on silica using isopropyl acetate. The first product eluted (2.27 g, yellow solid, m.p. 184°–186° C.) was identified as ethyl 5,8-bis(benzylthio)-1-cyclopropyl-7-(2,6-dimethyl-4-pyridinyl)-6-fluoro-1,4-dihydro-4-oxo-3-quinolinecarboxylate. The second product eluted (2.12 g, pale yellow solid, m.p. 190°–195° C.) was identified as the desired ethyl 1-cyclopropyl-6,8-difluoro-7-(2,6-dimethyl-4-pyridinyl)-5-(benzylthio)-1,4-dihydro-4-oxo-3-quinolinecarboxylate.

b) Ethyl 1-cyclopropyl-6,8-difluoro-7-(2,6-dimethyl-4-pyridinyl)-1,4-dihydro-4-oxo-3-quinolinecarboxylate [I; R=C$_2$H$_5$, R'=H, R"=F, Z=2,6-dimethyl-4-pyridinyl]

Raney nickel (10 g, wet) was rinsed with absolute ethanol and added to a suspension of 2.12 g ethyl 1-cyclopropyl-6,8-difluoro-7-(2,6-dimethyl-4-pyridinyl)-5-(benzylthio)-1,4-dihydro-4-oxo-3-quinolinecarboxylate in 100 ml of absolute ethanol. The mixture was heated at reflux for 15 min., then filtered and concentrated. The residue was chromatographed on silica gel using ethyl acetate to give 1.0 g ethyl 1-cyclopropyl-6,8-difluoro-7-(2,6-dimethyl-4-pyridinyl)-1,4-dihydro-4-oxo-3-quinolinecarboxylate, m.p. 186.5°–187° C.

c) 1-Cyclopropyl-6,8-difluoro-7-(2,6-dimethyl-4-pyridinyl)-1,4-dihydro-4-oxo-3-quinolinecarboxylic acid [I; R and R'=H, R"=F, Z=2,6-dimethyl-4-pyridinyl]

A suspension of 1.0 g ethyl 1-cyclopropyl-6,8-difluoro-7-(2,6-dimethyl-4-pyridinyl)-1,4-dihydro-4-oxo-3-quinolinecarboxylate in 20 ml 1M hydrochloric acid was heated at reflux for 2 hours. The reaction mixture was cooled, poured into saturated sodium acetate and extracted with ethyl acetate. The extract was dried (sodium sulfate) and concentrated, and the residue (0.84 g) was recrystallized from absolute ethanol to give 0.70 g 1-cyclopropyl-6,8-difluoro-7-(2,6-dimethyl-4-pyridinyl)-1,4-dihydro-4-oxo-3-quinolinecarboxylic acid, colorless needles, m.p. 246°–248.5° C.

A sample of the foregoing acid was converted to its sodium salt, obtained in the form of a yellow powder, m.p. above 300° C.

The methyl ester of the foregoing acid, pale yellow solid, m.p. 227°–228° C., was prepared by treating the free acid with N,N'-carbonyldiimidazole in dimethylformamide solution, then adding methanol and heating the mixture 3 hours at reflux.

EXAMPLE 6 a) Ethyl 1-cyclopropyl-6,8-difluoro-7-(2,6-dimethyl-4-pyridinyl)-5-(phenylthio)-1,4-dihydro-4-oxo-3-quinolinecarboxylate [I; R=C$_2$H$_5$, R'=C$_6$H$_5$S, R"=F, Z=2,6-dimethyl-4-pyridinyl] was prepared from 7.50 g ethyl 1-cyclopropyl-7-(2,6-dimethyl-4-pyridinyl)-5,6,8-trifluoro-1,4-dihydro-4-oxo-3-quinolinecarboxylate, 1.95 ml thiophenol and 0.92 sodium hydride in 190 ml tetrahydrofuran according to the procedure of Example 5, part (a), and was obtained in 80% yield as a light yellow solid, m.p. 230°–231° C. (from acetonitrile).

b) Ethyl 1-cyclopropyl-6,8-difluoro-7-(2,6-dimethyl-4-pyridinyl)-1,4-dihydro-4-oxo-3-quinolinecarboxylate [I; R=C$_2$H$_5$, R'=H, R"=F, Z=2,6-dimethyl-4-pyridinyl] was prepared from 2.5 g ethyl 1-cyclopropyl-6,8-difluoro-7-(2,6-dimethyl-4-pyridinyl)-5-(phenylthio)-1,4-dihydro-4-oxo-3-quinolinecarboxylate and 25 g Raney nickel in ethanol according to the procedure of Example 5, part (b), and was obtained in 86% yield, m.p. 185°–187° C., identical with the product of Example 5, part (b).

c) 1-Cyclopropyl-7-(2,6-dimethyl-4-pyridinyl)-6,8-difluoro-5-(phenylthio)-1,4-dihydro-4-oxo-3-quinolinecarboxylic acid [I; R=H, R'=C$_6$H$_5$S, R"=F, Z=2,6-dimethyl-4-pyridinyl] was prepared by hydrolysis of ethyl 1-cyclopropyl-6,8-difluoro-7-(2,6-dimethyl-4-pyridinyl)-5-(phenylthio)-1,4-dihydro-4-oxo-3-quinolinecarboxylate with hydrochloric acid according to the procedure of Example 5, part (c), and was obtained in the form of a light-yellow solid, m.p. 246.5°–247.5° C. (from acetonitrile).

EXAMPLE 7

1-Cyclopropyl-7-(2,6-dimethyl-4-pyridinyl)-6-fluoro-1,4-dihydro-4-oxo-8-(benzylthio)-3-quinolinecarboxylic acid [I; R and R'=H, R"=C$_6$H$_5$CH$_2$S, Z=2,6-dimethyl-4-pyridinyl] was obtained by treatment of ethyl 5,8-bis(benzylthio)-1-cyclopropyl-7-(2,6-dimethyl-4-pyridinyl)-6-fluoro-1,4-dihydro-4-oxo-3-quinolinecarboxylate (the byproduct obtained in Example 5, part a) with Raney nickel according to the procedure of Example 5, part (b), followed by hydrolysis of the resulting ester with hydrochloric acid according to the procedure of Example 5, part (c), and was obtained as a colorless solid, m.p. 207°–208° C. when recrystallized from ethanol.

EXAMPLE 8 a) 2,3,4,5-Tetrafluorobenzoyl chloride

Thionyl chloride (2.9 L), 2.5 kg 2,3,4,5-tetrafluorobenzoic acid and 14.5 ml dimethylformamide were charged to a 12 L reaction vessel and warmed at 90°–95° C. for about 90 minutes. The excess thionyl chloride was first removed at atmospheric pressure, then in vacuo. The residue was distilled on a steam bath at water pump pressure collecting the fraction with b.p. 65°–70° C. at about 15 mm resulting in 2635 g (96.2%) of pale yellow distillate.

b) Ethyl 2,3,4,5-tetrafluorobenzoylacetate

In a nitrogen atmosphere a 50 gallon kettle was charged with 50.9 kg of tetrahydrofuran, 5.2 kg of monoethyl malonate and about 5 g of 2,2'-dipyridyl. After cooling the mixture to −36° C., 41.6 kg of n-butyllithium (15% in hexane) was added over 3 hours maintaining the temperature at −25° to −35° C. The resultant slurry was cooled further to −60° C. and then treated over about 50 minutes with the acid chloride of part (a) at −62° to −54° C. The green/yellow mixture was stirred for 2 hours at ambient temperature and allowed to warm further overnight. The mixture (−24° C.) was quenched (vacuum) into ambient dilute hydrochloric acid (15 L of muriatic acid and 61 L of deionized water). The quench mixture was separated and the organic phase was washed with 2×40 L of deionized water. The combined aqueous phases were back extracted with 40 L of hexane-ether (1:1). All organic layers were combined and washed with 100 L of saturated sodium bicarbonate solution; again back extracting the aqueous phase with 40 L of hexane-ether (1:1). The combined organic layers were concentrated to an oil in vacuo followed by dissolution in 20 L of hexane and repeated concentration to dryness. The hot oil was finally dissolved in 19 L of hexane. The solution was cooled to −5° C. and the crystallized solids were filtered using 4.8 L of cold (−6° C.) hexane as wash. The material was dried in vacuo at room temperature affording 4234 g of product suitable for use in the next step. A second crop was obtained by concentrating the combined filtrate and wash and cooling to low temperature.

The combined yield for the first and second crops was 4841 g (74.9%).

c) Ethyl 1-cyclopropyl-6,7,8-trifluoro-1,4-dihydro-4-oxo-3-quinolinecarboxylate [XV; Alk=Et]

A 12 L stirred flask was charged with 4.8 L of tetrahydrofuran, 1584 g of ethyl 2,3,4,5-tetrafluorobenzoylacetate and 834 ml of dimethylformamide dimethyl acetal. After establishing a nitrogen atmosphere, this mixture was heated to reflux for 1 hour and then stirred at ambient temperature for four hours. The mixture was cooled and maintained at 4°-5° C. while adding 438 ml of cyclopropylamine over a period of 35 minutes. It was then stirred at 3°-5° C. for 1 hour and concentrated in vacuo. The yellow crystalline solid was dissolved in 3.6 L of dimethylformamide and 912 g of powdered potassium carbonate was added with strong stirring. The slurry was then heated on a steam bath for 1 hour (maximum internal temperature was 108° C. for 5 minutes). The hot mixture was poured into 30 L of cold water. Filtration, washing first with 6 L of cold water and then 6 L of cold ethanol followed by drying in vacuo at 50° C. gave 1615 g of product (86.5% yield).

d) Ethyl 7-azido-1-cyclopropyl-6,8-difluoro-1,4-dihydro-4-oxoquinolinecarboxylate [XVI; Alk=Et]

Dimethylformamide (2638 ml), 807 g of the ethyl cyclopropyl ester of part (c) and 177.3 g of sodium azide were combined and heated in a 12 L flask at 90°-95° C. for 2 hours. The resulting dark solution was allowed to cool slightly. The solution was diluted (vacuo) with 9 L of deionized water using an additional 8.7 L of deionized water to wash and transfer the thick slurry. The crystalline solid was collected and washed with 6.0 L of deionized water at room temperature. It was dried in vacuo at 50°-55° C. resulting in 809 g (93.4%) of tan material.

e) Ethyl 7-amino-1-cyclopropyl-6,8-difluoro-1,4-dihydro-4-oxo-3-quinolinecarboxylate [XVII; Alk=Et]

A slurry of 1.20 kg of ethyl 7-azido-1-cyclopropyl-6,8-difluoro-1,4-dihydro-4-oxo-3-quinolinecarboxylate in 12 L of dimethylformamide was charged to a five gallon autoclave. After placing the vessel under nitrogen, a slurry of 76 g of 10% palladium-on-carbon in 700 ml of dimethylformamide was added. The mixture was hydrogenated at 48-50 p.s.i. and 600 r.p.m. for four hours. The reaction mixture was filtered and concentrated under aspirator pressure to give a thick but stirrable dark residue. Ethanol (3 L) was added and the suspension was briefly refluxed before allowing to cool. After cooling to 5° C., the product was collected, washed with 2×500 ml of cold ethanol and then dried at 65°-70° C. in vacuo overnight to give 962 g (86.7%) of product.

f) Ethyl 7-bromo-1-cyclopropyl-6,8-difluoro-1,4-dihydro-4-oxoquinoline-3-carboxylate [XVIII; Alk=Et]

A 22 L flask was charged with 960 g of ethyl 7-amino-1-cyclopropyl-6,8-difluoro-1,4-dihydro-4-oxo-3-quinolinecarboxylate, 8.7 L of acetonitrile and 835 g of cupric bromide and heated to 70° C. N-Butyl nitrite (545 ml) was added over 30 minutes and the reaction mixture was heated at reflux for 2 hours. It was concentrated in vacuo until about 6 L of distillate was collected. The concentrate was poured into 19 L of 2 molar hydrochloric acid to form a precipitate. After stirring for 30 minutes the product was collected and washed with 4.0 L of deionized water, 12 L of 3.75 molar ammonium hydroxide and finally with an additional 12 L of deionized water. After drying in vacuo at 60° C. a total of 984 g (85.1%) of crude bromo compound was obtained. The crude product was dissolved in refluxing methanol and cooled slowly to 2° C. The solids were collected, washed with 2×350 ml of cold methanol and dried in vacuo at 50°-55° C. to afford a first crop of 598.5 g (60.8%).

g) Ethyl 1-cyclopropyl-6,8-difluoro-1,4-dihydro-7-(2,6-dimethyl-4-pyridinyl)-4-oxo-3-quinolinecarboxylate [I; Alk=Et, R'=H, R"=F, Z=2,6-dimethyl-4-pyridinyl]

A 5 L flask was charged with 590 g of ethyl 7-bromo-1-cyclopropyl-6,8-difluoro-1,4-dihydro-4-oxo-3-quinolinecarboxylate, 689 g of 2,6-dimethyl-4-(tributylstannyl)pyridine, 33.6 g of dichlorobis(triphenylphosphine) palladium catalyst and 375 ml of dimethylformamide under nitrogen, and heated slowly until the reaction began to exotherm at 130° C. At 140° C. the heater was removed and the temperature rose to 155° C. After the exotherm had subsided, the solution was heated at reflux for one hour. The cooled reaction mixture was dissolved in a chloroform (3.2 L)-water (2.6 L) mixture and filtered through Super-Cel to remove the spent catalyst. The filter cake was washed with 2×500 ml of chloroform and 1.0 L of water. The lower organic layer was separated and dried over magnesium sulfate. The drying agent was filtered and washed with 500 ml of chloroform. The filtrate was concentrated in vacuo to form a crystalline solid which was slurried in 3.5 L of hexane. The solid was collected and washed with more hexane (700 ml) and reslurried in 2.6 L of ether. The product was finally filtered, washed with 2.0 L of ether and air dried under a hood to give 512 g (80.7% yield) of product.

h) 1-Cyclopropyl-7-(2,6-dimethyl-4-pyridyl)-6,8-difluoro-1,4-dihydro-4-oxo-3-quinolinecarboxylic acid [I; R and R'=H, R"=F. Z=2,6-dimethyl-4-pyridinyl]

A suspension of 550 g of the ester of part (g) in 7.0 L of 1 molar hydrochloric acid was stirred on a steam bath for 2.5 hours to give a clear solution. The hot solution was treated with 30 g of charcoal and filtered. The yellow filtrate was cooled to room temperature and washed once with 3.0 L of chloroform to remove nonbasic impurities. The aqueous layer was diluted with 5 L of water, made strongly alkaline with 35% sodium hydroxide (pH 11-12) and warmed on a steam bath to 40° C. for two hours. At the end of this period an excess of acetic acid (280 ml) was added and the reaction mixture was warmed to 60°-70° C. on a steam bath for 4-6 hours. It was cooled to 40° C. and filtered, washed with 4 L of water and the white solid was dried at 65°-70° C. for 24 hours under vacuum to give 397 g (78%) of crude product. The crude product from four batches was combined and the total solids (1038 g) were crystallized from a mixture of 2.5 L of chloroform and 5.5 L of ethanol. Two crops were collected to give 980 g (94%) of pure product, identical with the product of Example 5(c).

EXAMPLE 9

1-Cyclopropyl-6-fluoro-1,4-dihydro-7-(2-methyl-4-pyridinyl)-4-oxo-3-quinolinecarboxylic acid [I; R, R' and R"=H, Z=2-methyl-4-pyridinyl] was prepared from ethyl 7-bromo-1-cyclopropyl-6-fluoro-1,4-dihydro-4-oxo-3-quinolinecarboxylate, 2-methyl-4-(trimethylstannyl)pyridine (prepared from 4-bromo-2-methylpyridine and trimethyltin chloride) and dichlorobis(triphenylphosphine)palladium in ethanol solution, heated 5 hrs. in an autoclave, and the resulting crude ester hydrolyzed with 2N hydrochloric acid, and was obtained in the form of a tan powder, m.p. 287°-288° C. (decompn.) when recrystallized from dimethylformamide.

According to the procedures described hereinabove, the following compounds were prepared:

EXAMPLE 10

1-Cyclopropyl-7-(2,6-dimethyl-3-pyridinyl)-6-fluoro-1,4-dihydro-4-oxo-3-quinolinecarboxylic acid [I; R, R' and R"=H, Z=2,6-dimethyl-3-pyridinyl], tan powder, m.p. 243°-244° C. when recrystallized from acetonitrile.

EXAMPLE 11

1-Cyclopropyl-6-fluoro-1,4-dihydro-4-oxo-7-(2,3,6-trimethyl-4-pyridinyl)-3-quinolinecarboxylic acid [I; R, R' and R"=H, Z=2,3,6-trimethyl-4-pyridinyl] light tan powder, m.p. 297°-298° C. when recrystallized from acetonitrile.

EXAMPLE 12

1-Cyclopropyl-7-(2-ethyl-4-pyridinyl)-6-fluoro-1,4-dihydro-4-oxo-3-quinolinecarboxylic acid [I; R, R' and R"=H, Z=2-ethyl-4-pyridinyl], colorless powder, m.p. 286°-288° C. when recrystallized from acetonitrile.

EXAMPLE 13

1-Cyclopropyl-6-fluoro-7-(6-methyl-3-pyridinyl)-1,4-dihydro-4-oxo-3-quinolinecarboxylic acid [I; R, R' and R"=H, Z=6-methyl-3-pyridinyl], colorless powder, m.p. 243°-245° C.(decompn.).

EXAMPLE 14

1-Cyclopropyl-6-fluoro-7-(5-methyl-3-pyridinyl)-1,4-dihydro-4-oxo-3-quinolinecarboxylic acid [I; R, R' and R"=H, Z=5-methyl-3-pyridinyl], colorless solid, m.p. 260°-264° C.

EXAMPLE 15 a) 1,5-Di(trifluoromethyl)-1,3,5-trioxopentane [$F_3CCOCH_2COCH_2COCF_3$]

To 36 g of sodium hydride (60% dispersion) in 350 ml dioxane at reflux was added dropwise a solution of 10.4 g acetone and 76.7 g ethyl trifluoroacetate in 350 ml dimethylformamide over a period of 30 minutes. The reaction mixture was heated at reflux for 16 hrs., then cooled in ice and 6 ml ethanol and 6 ml water added. The solvent was removed in vacuo and the residue partitioned between ether and water. The ether layer was extracted with water and dilute sodium hydroxide and the combined aqueous extracts acidified with hydrochloric acid. The latter mixture was extracted with ether, dried ($MgSO_4$), concentrated in vacuo and distilled to give 30 g 1,5-di(trifluoromethyl)-1,3,5-trioxopentane, b.p. 65°-70° C. (35 mm.).

b) 2,6-Di(trifluoromethyl)-4-hydroxypyridine

A mixture of 30 g 1,5-di(trifluoromethyl)-1,3,5-trioxopentane and 125 ml 28% aqueous ammonium hydroxide was heated in an autoclave at 130° C. for 5 hours. The reaction mixture was concentrated in vacuo, dissolved in 350 ml ethanol and treated with 11 ml 6N hydrochloric acid. The resulting mixture was concentrated in vacuo, 100 ml water added to the residue and filtered to give 8.0 g 2,6-di(trifluoromethyl)-4-hydroxypyridine, m.p. 123°-130° C.

c) 4-Bromo-2,6-di(trifluoromethyl)pyridine

A mixture of 6 g 2,6-di(trifluoromethyl)-4-hydroxypyridine and 4.9 ml phosphorus tribromide was heated 15 min. at 140°-150° C. and 90 min. at 160°-170° C. The reaction mixture was cooled, 150 ml methylene dichloride added, and poured into ice-water. From the methylene dichloride layer there was isolated 3.5 g 4-bromo-2,6-di(trifluoromethyl)pyridine, colorless solid, m.p. 92°-95° C.

d) 2,6-Di(trifluoromethyl)-4-(trimethylstannyl)pyridine was prepared from 8.7 g 4-bromo-2,6-di(trifluoromethyl)pyridine, 12.4 ml butyllithium (24M in hexane) and 6 g trimethyltin chloride in 200 ml ether according to the procedure of Example 3, part (g), and was obtained (11 g) as a yellow semi-solid.

e) Ethyl 1-cyclopropyl-6-fluoro-7-[2,6-di(trifluoromethyl)-4-pyridinyl]-1,4-dihydro-4-oxo-3-quinolinecarboxylate was prepared from 4 g 7-bromo-1-cyclopropyl-6-fluoro-1,4-dihydro-4-oxo-3-quinolinecarboxylate, 5 g 2,6-di(trifluoromethyl)-4-(trimethylstannyl)pyridine, 400 mg dichlorobis(triphenylphosphine)palladium and 2 ml HMPA in 60 ml dioxane according to the procedure of Example 1, part (h), and was obtained (2.8 g) as a solid with m.p. 239°-241° C.

f) 1-Cyclopropyl-6-fluoro-7-[2,6-di(trifluoromethyl)-4-pyridinyl]-1,4-dihydro-4-oxo-3-quinolinecarboxylic acid [I; R, R' and R"=H, Z=2,6-di(trifluoromethyl)-pyridinyl] was prepared by hydrolysis of the ethyl ester of part (e) with sodium hydroxide in aqueous methanol, and was obtained in 87% yield as a colorless solid, m.p. above 300° C. when recrystallized from methanol.

EXAMPLE 16 a) Ethyl 1-cyclopropyl-7-(2,6-dimethyl-4-pyridinyl)-6-fluoro-1,4-dihydro-4-oxo-3-quinolinecarboxylate N(Py)-oxide m-Chloroperbenzoic acid (85%, 282 mg) was added to a stirred mixture of 0.5 g ethyl 1-cyclopropyl-7-(2,6-dimethyl-4-pyridinyl)-6-fluoro-1,4-dihydro-4-oxo-3-quinolinecarboxylate and 12 ml methylene dichloride. The reaction mixture was stirred at room temperature for 2 hours, then concentrated and the residue treated with saturated sodium bicarbonate solution. The solid product was collected, washed with water and dried to give 0.47 g ethyl 1-cyclopropyl-7-(2,6-dimethyl-4-pyridinyl)-6-fluoro-1,4-dihydro-4-oxo-3-quinolinecarboxylate N(Py)-oxide, m.p. 250°-255° C.

b) 1-Cyclopropyl-7-(2,6-dimethyl-4-pyridinyl)-6-fluoro-1,4-dihydro-4-oxo-2-quinolinecarboxylic acid N(Py)-oxide [I; R, R' and R"=H, Z=2,6-dimethyl-4-pyridinyl N-oxide]

A mixture of 2.5 g ester of part (a) and 646 mg sodium hydroxide in 68 ml water was heated at reflux for three hours. The reaction mixture was filtered and acidified with acetic acid. The solid product was collected, washed with water and dried to give 1.7 g 1-cyclopropyl-7-(2,6-dimethyl-4-pyridinyl)-6-fluoro-1,4-dihydro-4-oxo-2-quinolinecarboxylic acid N(Py)-oxide, m.p. 314° C. (decompn.) when recrystallized from dimethylformamide.

EXAMPLE 17 a) Ethyl 7-[2-(acetoxymethyl)-6-methyl-4-pyridinyl]-1-cyclopropyl-6-fluoro-1,4-dihydro-4-oxo-3-quinolinecarboxylate [I; R=$C_2H_5$, R' and R"=H, Z=2-acetoxymethyl-6-methyl-4-pyridinyl]

Ethyl 1-cyclopropyl-7-(2,6-dimethyl-4-pyridinyl)-6-fluoro-1,4-dihydro-4-oxo-3-quinolinecarboxylate N(Py)-oxide (Example 16a) (3 g) was added portionwise to 10 ml refluxing acetic anhydride. The reaction mixture was heated at reflux for 30 min., then cooled, ethanol added and concentrated in vacuo. Ether was added to the residue and the solid product collected (3.2 g).

b) 1-Cyclopropyl-6-fluoro-7-[2-(hydroxymethyl)-6-methyl-4-pyridinyl]-1,4-dihydro-4-oxo-3-quinolinecarboxylic acid [I; R, R' and R"=H, Z=2-(hydroxymethyl)-6-methyl-4-pyridinyl]

The ester of part (a) (1.5 g) in 30 ml of 6N hydrochloric acid was heated under reflux for 2 hours. The reaction mixture was cooled, concentrated ammonium hydroxide added until a clear solution resulted, and acidified with acetic acid. The solid product (0.92 g) was collected and recrystallized from ethanol to give 1-cyclopropyl-6-fluoro-7-[2-(hydroxymethyl)-6-methyl-4-pyridinyl]-1,4-dihydro-4-oxo-3-quinolinecarboxylic acid, light tan powder, m.p. 270°–272° C.(decompn.).

EXAMPLE 18 a) Ethyl 1-cyclopropyl-6-fluoro-7-[2-(hydroxymethyl)-6-methyl-4-pyridinyl]-1,4-dihydro-4-oxo-3-quinolinecarboxylate Ethanolic hydrogen chloride (150 ml) was added to a suspension of 7.5 g ethyl 7-[2-(acetoxymethyl)-6-methyl-4-pyrindyl]-1-cyclopropyl-6-fluoro-1,4-dihydro-4-oxo-3-quinolinecarboxylate (Example 17a) in 200 ml absolute ethanol, and the mixture heated at reflux for 90 min. The reaction mixture was concentrated in vacuo to give 6.68 g ethyl 1-cyclopropyl-6-fluoro-7-[2-hydroxymethyl)-6-methyl-4-pyridinyl]-1,4-dihydro-4-oxo-3-quinolinecarboxylate in the form of its hydrochloride salt, m.p. 240° C.(decompn.).

b) Ethyl 1-cyclopropyl-7-[2-(chloromethyl)-6-methyl-4-pyridinyl]-6-fluoro-1,4-dihydro-4-oxo-3-quinolinecarboxylate [I; R=C₂H₅, R' and R"=H, Z=2-(chloromethyl)-6-methyl-4-pyridinyl]

Ethyl 1-cyclopropyl-6-fluoro-7-[2-(hydroxymethyl)-6-methyl-4-pyridinyl]-1,4-dihydro-4-oxo-3-quinolinecarboxylate hydrochloride (6.68 g) in 40 ml thionyl chloride was heated at reflux for two hours. The excess thionyl chloride was removed in vacuo and by repeatedly adding ethanol and concentrating. The residue was crystallized from ethanol to give 5.50 g ethyl 1-cyclopropyl-7-[2-(chloromethyl)-6-methyl-4-pyridinyl]-6-fluoro-1,4-dihydro-4-oxo-3-quinolinecarboxylate as its hydrochloride salt.

c) 1-Cyclopropyl-7-[2-(ethylaminomethyl)-6-methyl-4-pyridinyl]-6-fluoro-1,4-dihydro-4-oxo-3-quinolinecarboxylic acid [I; R, R' and R"=H, Z=2-(ethylaminomethyl)-6-methyl-4-pyridinyl]

A mixture of 1.1 g ethyl 1-cyclopropyl-7-[2-(chloromethyl)-6-methyl-4-pyridinyl]-6-flouro-1,4-dihydro-4-oxo-3-quinolinecarboxylate hydrochloride, 5 ml water and 10 ml methylene dichloride was treated while stirring in an ice-bath with 5 ml 70% ethylamine. The reaction mixture was stirred at room temperature for about 16 hours, and then extracted with methylene dichloride, dried (MgSO₄) and concentrated. The residue (1 g) was repeatedly subjected to plate chromatography developed with 3% isopropyl acetate in ethyl acetate, and the resulting ethyl ester of the desired product (760 mg) hydrolyzed with 6N hydrochloric acid (3 hours under reflux) to give 1-cyclopropyl-7-[2-(ethylaminomethyl)-6-methyl-4-pyridinyl]-6-fluoro-1,4-dihydro-4-oxo-3-quinolinecarboxylic acid in the form of its hydrochloride salt, m.p. 277° C.(decompn.) when recrystallized from ethanol.

By replacing the ethylamine in the foregoing procedure by a molar equivalent amount of ammonia, it is contemplated that there can be obtained 1-cyclopropyl-7-[2-(aminomethyl)-6-methyl-4-pyridinyl]-6-fluoro-1,4-dihydro-4-oxo-3-quinolinecarboxylic acid [I; R, R' and R"=H, Z=2-(aminomethyl)-6-methyl-4-pyridinyl].

EXAMPLE 19

1-Cyclopropyl-7-[2-(dimethylaminomethyl)-6-methyl-4-pyridinyl]-6-fluoro-1,4-dihydro-4-oxo-3-quinolinecarboxylic acid [I; R, R' and R"=H, Z=2-(dimethylaminomethyl)-6-methyl-4-pyridinyl] was prepared according to the procedure of Example 18, part (b), replacing the ethylamine by a molar equivalent amount of dimethylamine, and was obtained in the form of its hydrochloride salt, m.p. 259°–262° C.(decompn.) when recrystallized from ethanol/ether.

EXAMPLE 20

1-Cyclopropyl-6-fluoro-7-[2-(methylaminomethyl)-6-methyl-4-pyridinyl]-1,4-dihydro-4-oxo-3-quinolinecarboxylic acid [I; R, R' and R"=H, Z=2-(methylaminomethyl)-6-methyl-4-pyridinyl] was prepared according to the procedure of Example 18, part (b), replacing the ethylamine by a molar equivalent amount of methylamine, and was obtained in the form of its hydrochloride salt, m.p. 262°–265° C. when recrystallized from ethanol.

EXAMPLE 21

1-Cyclopropyl-6-fluoro-7-[2-(methoxymethyl)-6-methyl-4-pyridinyl]-1,4-dihydro-4-oxo-3-quinolinecarboxylic acid [I; R, R' and R"=H, Z=2-(methoxymethyl)-6-methyl-4-pyridinyl]

A solution of 1.52 g ethyl-1-cyclopropyl--7-[2-(chloromethyl)-6-methyl-4-pyridinyl]-6-fluoro-1,4-dihydro-4-oxo-3-quinolinecarboxylic acid (Example 18b) in 125 ml methanol was treated with 1.5 g of powdered sodium methoxide, and the reaction mixture was heated at reflux for about 16 hours. The mixture was quenched in ice containing acetic acid and extracted with methylene dichloride. The extracts were concentrated and the residue treated with water. The solid product was collected and dried (1.11 g) and was recrystallized from ethyl acetate/hexane to give 0.91 g 1-cyclopropyl-6-fluoro-7-[2-(methoxymethyl)-6-methyl-4-pyridinyl]-1,4-dihydro-4-oxo-3-quinolinecarboxylic acid, m.p. 192°–193° C.

The in vitro antimicrobial activity of the compounds of the invention was determined by a microplate dilution procedure. Bacterial cultures were grown in Meuller Hinton II (cation supplemented) broth (*S. aureus, S. faecalis, M. luteus, E. coli* and *P. aeruginosa*), Brain Heart Infusion (BHI) broth supplemented with 10% heat inactivated horse serum (*S. pneumoniae*) or BHI broth supplemented with 5 mcg/ml Hemin and 0.5 mcg/ml vitamin K (*B. fragilis*) at 37° C. for 18–24 hrs. The cultures were produced under aerobic conditions with the exception of *B. fragilis* which was grown 48 hrs. under anaerobic conditions (atmosphere 5% $CO_2$, 10% $H_2$ and 85% $N_2$). Resulting suspensions were diluted 1/10 in the appropriate broth or used undiluted for the inoculum. Aqueous solutions of the compounds of the invention were solubilized in dimethylsulfoxide (DMSO) at the desired concentration and 200 mcl were dispensed into the first row of wells of a sterile microplate. The compounds were then serially diluted twofold in DMSO to give a working stock concentration range plate. The last row of wells was left compound-free receiving only DMSO to serve as a growth control. Five mcl from each well of the working stock plate was transferred to corresponding wells of a separate plate containing 95 mcl/well of the appropriate broth. All dilutions were made with either an automated dilutor or manually. The wells of microplate containing the desired compound concentrations and compound-free growth controls in broth were then inoculated using the MIC 2000 inoculator which delivers 1.5 mcl/well to give a final inoculum level of $10^4$ microorganism/well or $10^5$ microorganism/ml. Plates were incubated as described above and read for visible growth. The minimal inhibitory concentration (MIC: expressed in mcg/ml) of each compound tested against each test microorganism was determined as the lowest concentration of compound which prevents visible microbial growth.

The following compounds were tested according to the foregoing procedure:

A. 1-Cyclopropyl-7-(2,6-dimethyl-4-pyridinyl)-6-fluoro-1,4-dihydro-4-oxo-3-quinolinecarboxylic acid (Examples 1i and 2f).

B. 1-Cyclopropyl-7-(2,6-dimethyl-4-pyridinyl)-5,6,8-trifluoro-1,4-dihydro-4-oxo-3-quinolinecarboxylic acid (Example 4g).

C. 1-Cyclopropyl-6,8-difluoro-7-(2,6-dimethyl-4-pyridinyl)-1,4-dihydro-4-oxo-3-quinolinecarboxylic acid (Example 5c).

Prior art compounds:

P. 7-(2,6-Dimethyl-4-pyridinyl)-1-ethyl-1,4-dihydro-4-oxo-3-quinolinecarboxylic acid.

Q. 1-Cyclopropyl-6-fluoro-7-(1-piperazinyl)-1,4-dihydro-4-oxo-3-quinolinecarboxylic acid.

R. 7-(2,6-Dimethyl-4-pyridinyl)-1-ethyl-6-fluoro-1,4-dihydro-4-oxo-3-quinolinecarboxylic acid.

The following Table I summarizes the results of the testing of the foregoing compounds:

TABLE I

| Compound | In vitro (mcg/ml) | | | | | | |
|---|---|---|---|---|---|---|---|
| | ML MIC | EC MIC | SA MIC | SF MIC | SP MIC | PA MIC | BF MIC |
| A | 0.5 | 0.03 | 0.008 | 0.06 | 0.03 | 2 | 0.5 |
| B | 0.5 | 0.125 | 0.008 | 0.06 | 0.03 | 8 | 0.5 |
| C | 0.25 | 0.06 | 0.008 | 0.06 | 0.016 | 4 | 0.125 |
| P | 8 | 0.25 | 0.25 | 1 | 2 | 32 | 16 |
| Q | 2 | 0.004 | 0.25 | 0.5 | 0.25 | 0.125 | 2 |
| R | 0.5 | 0.06 | 0.03 | 0.25 | 0.25 | 4 | 2 |

ML = *Micrococcus luteus*
EC = *Escherichia coli*
SA = *Staphylococcus aureus*
SF = *Streptococcus faecalis*
SP = *Streptococcus pneumoniae*
PA = *Pseudomonas aeruginosa*
BF = *Bacteroides fragilis*

It will be seen from the above Table that the compounds of the invention (A, B, C) are substantially more active than the prior art compounds (P, Q, R) against all of the organisms except *E. coli* and *P. aeruginosa*, and except *M. luteus* in the case of compound R. The improvement in activity is particularly marked in the case of the important pathogen *Staph. aureus*, where compounds A, B and C are thirty times as active as compounds P and Q and four times as active as compound R.

The in vivo antibacterial activity of the compounds of the invention was determined in female mice, 18-20 grams each. Aqueous solutions of the compounds to be tested were prepared by dissolving the free acid form in dilute sodium hydroxide and diluting the solution with distilled water to the desired concentration.

Cultures of *E. coli* were grown in brain heart infusion broth, and the mice were inoculated intraperitoneally with 0.5 ml of the bacterial test inoculum suspended in saline. Cultures of *Staph. aureus* were thawed from frozen pooled stocks and mixed with 5% mucin. A 0.5 ml preparation was used to infect mice by i.p. inoculation.

The mice were medicated subcutaneously (sc) or orally (po) with 0.5 ml of the test compound solution one-half hour postinfection. Deaths were recorded daily for seven days. Fifty percent protective dose values ($PD_{50}$) were calculated using probit analysis. The results are given in the following Table II.

TABLE II

| | In vivo (Mouse, mg/kg) | | | |
|---|---|---|---|---|
| | Staph. aureus ($PD_{50}$) | | E. coli ($PD_{50}$) | |
| Compound | sc | po | sc | po |
| A | 0.08 | 0.20 | 3.1 | 3.8 |
| B | 0.08 | 0.14 | 8.9 | 10.8 |
| C | 0.06 | 0.09 | 6.1 | 5.7 |
| P | 2.37 | 3.8 | 13.5 | 17.9 |
| Q | 1.16 | 5.9 | 0.09 | 0.57 |
| R | 0.71 | 1.38 | 5.39 | 8.24 |

It will be seen from the above Table II that, although the compounds of the invention (A, B, C) are about equal in activity to compounds P and R and less active than compound Q against *E. coli*, the new compounds are markedly more active (9-30 times) than the prior art compounds against *Staph. aureus*.

In monkeys, compounds A and C gave high and prolonged serum levels after 25 mg/kg oral dosing. Compound A showed a maximum concentration of 13 µg/ml at 7 hours with a half-life of 13 hours; and compound C showed a maximum concentration of 34 µg/ml at 5.5 hours with a half-life of 20 hours.

The compound of Example 6(c), 1-cyclopropyl-7-(2,6-dimethyl-4-pyridinyl)-6,8-difluoro-5-(phenylthio)1,4-dihydro-4-oxo-3-quinolinecarboxylic acid, also was found to have appreciable antibacterial activity in vitro, MIC (µg/ml) values as follows: *M. luteus* (16.0), *Staph. aureus* (1.0), *Strep. faecalis* (16.0), *Strep. pneumoniae* (2.0), and *B. fragilis* (16.0).

The compound of Example 7, 1-cyclopropyl-7-(2,6-dimethyl-4-pyridinyl)-6-fluoro-1,4-dihydro-4-oxo-8-(benzylthio)-3-quinolinecarboxylic acid, also was found to have appreciable antibacterial activity in vitro, MIC (µg/ml) values as follows: *M. luteus* (64.0), *E. coli* (4.0), *Staph. aureus* (<0.125), *Strep. faecalis* (2.0), *Strep. pneumoniae* (2.0) and *B. fragilis* (64.0).

Table III below gives the in vitro activity data for additional compounds within the scope of the invention.

TABLE III

| Compound of Example | In vitro (mcg/ml) | | | | | |
|---|---|---|---|---|---|---|
| | EC | SA | SF | SP | PA | BF |
| 9 | 0.03 | 0.016 | 0.06 | 0.06 | 2.0 | 0.5 |
| 10 | 0.5 | 1.0 | 4.0 | 8.0 | >16 | 4.0 |
| 11 | 0.125 | 0.06 | 0.5 | 0.25 | 8.0 | 4.0 |
| 12 | 0.125 | 0.03 | 0.25 | 0.25 | 4.0 | 1.0 |
| 13 | 0.03 | 0.06 | 0.25 | 0.125 | 4.0 | 0.25 |
| 14 | 0.06 | 0.016 | 0.125 | 0.06 | 2.0 | 0.25 |
| 15f | 0.5 | 0.125 | 1.0 | 1.0 | >16 | 8.0 |

TABLE III-continued

| Compound of Example | In vitro (mcg/ml) | | | | | |
|---|---|---|---|---|---|---|
| | EC | SA | SF | SP | PA | BF |
| 16b | 0.125 | 0.25 | 0.5 | 0.5 | 8.0 | 4.0 |
| 17b | 0.06 | 0.03 | 0.125 | 0.06 | 4.0 | 1.0 |
| 18c | 0.06 | 0.5 | 2.0 | 0.5 | 8.0 | 8.0 |
| 19 | 0.06 | 0.06 | 0.5 | 0.5 | 8.0 | 2.0 |
| 20 | ≦0.016 | 0.125 | 0.2 | 0.25 | 1.0 | 2.0 |
| 21 | 0.25 | 0.03 | 0.125 | 0.125 | 8.0 | 1.0 |

Selected compounds of the invention also possess topoisomerase II inhibition activity.

The compounds of the invention can be prepared for use by conventional pharmaceutical procedures; that is, by dissolving or suspending them in a pharmaceutically acceptable vehicle, e.g., water, aqueous alcohol, glycol, oil solution or oil-water emulsion, for parenteral or oral administration or topical application; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

We claim:

1. A compound having the formula

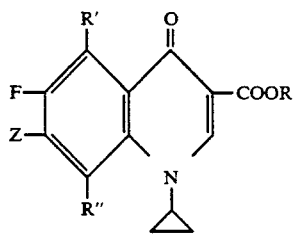

wherein:

R is hydrogen or lower-alkyl;

R' is selected from the group consisting of hydrogen, fluoro and —SR''', where R''' is phenyl, benzyl or lower-alkyl;

R'' is selected from the group consisting of hydrogen, fluoro and —SR''', with the proviso that when R'' is hydrogen, R' is also hydrogen, where in the definitions of R and R''', lower-alkyl, each occurrence, has from 1 to 6 carbon atoms;

Z is 2,6-dimethyl-4-pyridinyl;

a pharmaceutically acceptable acid-addition salt thereof; or an alkali metal or a pharmaceutically acceptable amine salt of a compound where R is hydrogen.

2. A compound according to claim 1 wherein R is hydrogen and R' and R'' are hydrogen or fluoro.

3. 1-Cyclopropyl-7-(2,6-dimethyl-4-pyridinyl)-5,6,8-trifluoro-1,4-dihydro-4-oxo-3-quinolinecarboxylic acid, according to claim 2.

4. 1-Cyclopropyl-7-(2,6-dimethyl-4-pyridinyl)-6-fluoro-1,4-dihydro-4-oxo-3-quinolinecarboxylic acid, according to claim 2.

5. 1-Cyclopropyl-6,8-difluoro-1,4-dihydro-7-(2,6-dimethyl-4-pyridinyl)-4-oxo-3-quinolinecarboxylic acid, according to claim 2.

6. 1-Cyclopropyl-7-(2,6-dimethyl-4-pyridinyl)-6,8-difluoro-1,4-dihydro-5-(phenylthio)-3-quinolinecarboxylic acid, according to claim 1.

7. 1-Cyclopropyl-7-(2,6-dimethyl-4-pyridinyl)-6-fluoro-1,4-dihydro-8-(benzylthio)-3-quinolinecarboxylic acid, according to claim 1.

8. A composition for combating bacteria, which comprises an antibacterially effective amount of a compound according to claim 1 where R is hydrogen together with one or more pharmaceutically acceptable excipients or diluents.

9. A method for combating bacteria, which comprises contacting the locus of said bacteria with a composition according to claim 8.

10. A method for combating a bacterial infection in a mammalian host which comprises administering to said host an antibacterially effective amount of a composition according to claim 8.

11. A composition for combating bacteria, which comprises an antibacterially effective amount of the compound according to claim 4 together with one or more pharmaceutically acceptable excipients or diluents.

12. A method for combating bacteria, which comprises contacting the locus of said bacteria with a composition according to claim 11.

13. A method for combating a bacterial infection in a mammalian host which comprises administering to said host an antibacterially effective amount of a composition according to claim 11.

* * * * *